United States Patent [19]

Herrmann

[11] 4,073,816
[45] Feb. 14, 1978

[54] PROCESS FOR THE CONTINUOUS PRODUCTION OF MONOCHLOROALKANES

[75] Inventor: Rudolf Herrmann, Homberg, Ndrh., Germany

[73] Assignee: Deutsche Texaco Aktiengesellschaft, Hamburg, Germany

[21] Appl. No.: 596,330

[22] Filed: July 16, 1975

[30] Foreign Application Priority Data

July 20, 1974  Germany ............................ 2435029

[51] Int. Cl.$^2$ ...................... C07C 17/16; C07C 23/10
[52] U.S. Cl. ............................ 260/648 R; 260/648 C; 260/657
[58] Field of Search ................ 260/657, 648 R, 648 C

[56] References Cited

U.S. PATENT DOCUMENTS

| | | | |
|---|---|---|---|
| 1,983,542 | 12/1934 | Holt et al. | 260/657 |
| 2,026,131 | 12/1935 | Klein et al. | 260/657 |
| 2,124,605 | 7/1938 | Bousquet | 260/657 |
| 2,396,639 | 3/1946 | Carter | 260/657 |
| 2,622,107 | 12/1952 | Mattson | 260/657 |
| 2,847,484 | 8/1958 | Kolker | 260/657 |
| 3,502,733 | 3/1970 | Kurtz et al. | 260/657 |

FOREIGN PATENT DOCUMENTS

| | | | |
|---|---|---|---|
| 691,295 | 7/1964 | Canada | 260/657 |
| 172,289 | 7/1965 | U.S.S.R. | 260/657 |
| 199,859 | 5/1966 | U.S.S.R. | 260/657 |

OTHER PUBLICATIONS

Meyer-Jacobson, "Lehrbuch der Organischen Chemie" *Zweite Auflage, Erster Band,* Allgemeiner Teil, Erster Teil, Leipzig (1907), p. 281.

*Primary Examiner*—Daniel E. Wyman
*Assistant Examiner*—Thomas A. Waltz
*Attorney, Agent, or Firm*—Thomas H. Whaley; Carl G. Ries; James J. O'Loughlin

[57] ABSTRACT

Monochloroalkanes are produced by reacting the corresponding alcohol with hydrogen chloride in the presence of a solution of zinc chloride. The mixture of alcohol and zinc chloride solution is saturated with gaseous hydrogen chloride and this mixture in a thin layer contacted with gaseous hydrogen chloride.

8 Claims, No Drawings

PROCESS FOR THE CONTINUOUS PRODUCTION OF MONOCHLOROALKANES

BACKGROUND OF THE INVENTION

Field of the Invention

It is known to produce monochloroalkanes or monochlorocycloalkanes by chlorination of the respective alkanes. However, in the chlorination process, all theoretically possible isomeric monochloroalkanes and also di- and polychloroalkanes are formed, so that a mixture of many chloroalkanes is obtained from which the individual chloroalkanes are not readily separated or are very difficult to separate.

The only possible way to bind the chlorine atom to a specific carbon atom in the molecule is to replace the hydroxyl group of the corresponding alcohol by chlorine, i.e. to practically esterize the alcohols. This reaction is best performed by reacting the pertinent alcohols with hydrogen chloride, preferably in the presence of catalysts at elevated temperatures. Suitable catalysts include for example, sulfuric acid, zinc chloride and copper sulfate. So far, the most favorable results have been obtained with zinc chloride in the form of aqueous solutions. But it is also possible to employ aqueous and/or alcoholic zinc chloride solutions.

One problem with this conventional process is that the zinc chloride catalyst, due to this dehydrating effect forms considerable amounts of ethers as well as olefins and tar. The conversion to monochloroalkane is far less than could be desired even if operating discontinuously.

Another problem with the conventional process relates to the separation of the catalyst from the reaction mixture and then separation of the monochloroalkanes or monochlorocycloalkane product from the by-products.

An object of the present invention is to provide a continuous process for the production of a monochloroalkane.

Another object is to provide a process which produces a relatively pure monochloroalkane thus preventing or reducing the problem of recovery from undesirable by-products.

A further object is to provide a process for the continuous production of a specific monochloroalkane as opposed to mixtures of monochloroalkanes.

Another object of the invention is to provide a process for continuously producing a specific monochloroalkane by chlorinating the corresponding aliphatic or cycloaliphatic alcohol.

SUMMARY OF THE INVENTION

The present invention relates to a process for the production of monochloroalkanes or monochlorocycloalkanes having more than four carbon atoms in the molecule in which the chlorine atom is bound to a specific carbon atom, by reacting the respective alcohols with hydrogen chloride in the presence of preferably concentrated aqueous zinc chloride solution as the catalyst. In general, this process is effective for producing monochloroalkanes and monochlorocycloalkanes having from 5 to 12 carbon atoms. According to the invention this process is operated continuously.

In this process of the invention, the alcohol is converted to a large extent at relatively low temperatures in a single passage, and only few by-products are formed, so that the chloroalkanes or chlorocycloalkanes obtained are rather pure and the crude chloroalkanes or chlorocycloalkanes can be separated from the catalyst without any difficulties. The effective reaction temperature range is from 60° to 97° C.

The respective alcohols are reacted with hydrogen chloride in the presence of aqueous zinc chloride solution as catalyst. According to the invention, the reaction is performed as follows: A hydrogen chloride-saturated solution comprising 1.5 to 3.0 parts by weight of a concentrated aqueous zinc chloride solution and 1 part by weight of alcohol is passed in a thin layer downward through a reactor having a large surface area at a temperature of at least 50° C and such an amount of gaseous hydrogen chloride is passed in countercurrent flow to the solution that an excess of hydrogen chloride of at least 5% (related to the quantity of hydrogen chloride which is required for the total conversion of the alcohol) is available for the reaction. By concentrated zinc chloride solution is meant a solution of at least 50% by weight zinc chloride up to a saturated zinc chloride solution.

The optimum ratio of zinc chloride solution to alcohol and the temperatures most favorable for a practically total conversion of alcohol must be established for each alcohol in short preliminary tests.

The raw chloroalkanes or cycloalkanes can easily be separated from the catalyst solution, as they form two layers. The raw chloroalkanes or cycloalkanes have a degree of purity from about 95–99% so that they may be used for many purposes without being further purified, e.g. for the production of metal organic compounds. Complete purification by distillation, however, does not represent any problem, as the small amounts of by-products practically comprise only olefins, ethers, and non-converted alcohols. If the catalyst has been diluted by the reaction water to such an extent (less than 50% $ZnCl_2$) that its activity is considerably reduced, it can be readily regenerated by reconcentrating it. This is best achieved by azeotropic distillation of the excessive water with alcohol. Normal-butanol has proven most effective. If necessary, the catalyst can be freed from colored impurities by extraction after or before it is reconcentrated.

Reactors with large surface areas suitable for this reaction include primarily heat exchangers or columns with trays of the most valid varied construction.

The monochloroalkanes or -cycloalkanes produced by the process of the invention are useful as solvents and also as raw materials for organic syntheses. They are especially suitable for the Friedel-Craft synthesis. The following examples illustrate the process of the present invention.

EXAMPLE 1

In a heat exchanger (inner diameter 100 mm, length 2000 mm) provided with a glass coil, a hydrogen chloride-saturated mixture comprising 2 parts by weight of a 70% aqueous zinc chloride solution and 1 part by weight of cyclohexanol is passed in a thin layer in downward direction through the tube of the heat exchanger while hydrogen chloride is flowing in countercurrent direction from the bottom. At the same time, the downward flowing reaction mixture is heated to 55° to 65° C by charging the glass coil with hot water. The hourly charge is 28 kg reaction mixture and 4 kg hydrogen chloride. The reaction mixture flowing off is collected in a separator where it immediately separates into two layers. The upper layer is the raw monochlorocyclohexane and the lower layer the zinc chloride catalyst. The monochlorocyclohexane has a concentration of 98 to 99%. The excessive hydrogen chloride (15 to 20%) is reused for saturating the catalyst alcohol mixture. The 1 to 2% of impurities of the monochlorocyclohexane comprise ethers, olefins, and non-converted cyclohexanol.

EXAMPLE 2

Following the procedure employed in Example 1, a hydrogen chloride-saturated reaction mixture comprising 19.6 kg of a 70% zinc chloride solution and 9.4 kg n-dodecanol is passed in a thin layer over the glass coil of the heat exchanger. The coil is charged with boiling water, thus heating the reaction mixture to 95° to 97° C, while 2.1 kg/h hydrogen chloride are passed in countercurrent flow to the reaction mixture. The hourly charge of hydrogen chloride-saturated reaction mixture is 28 kg per hour. The reaction product obtained contains 95 to 96% n-dodecyl chloride.

I claim:

1. In a method for the continuous production of a monochloroalkane or a monochlorocycloalkane which comprises reacting a monohydric alcohol with hydrogen chloride in the presence of a zinc chloride catalyst, said monohydric alcohol being selected from the group consisting of monohydric alkanols and monohydric cycloalkanols having above 4 and up to 12 carbon atoms and said catalyst consisting of an aqueous solution of zinc chloride consisting of at least 50 weight percent of zinc chloride, the improvement which comprises mixing said monohydric alcohol and said aqueous zinc chloride solution to form a liquid phase reaction mixture, saturating said reaction mixture with hydrogen chloride to form a liquid phase hydrogen chloride-saturated reaction mixture, passing said hydrogen chloride-saturated reaction mixture into a reactor to form a downwardly flowing thin layer of said liquid phase hydrogen chloride-saturated reaction mixture in said reactor, maintaining the temperature in said reactor above about 50° C, contacting said hydrogen chloride-saturated reaction mixture with a counter-current flow of hydrogen chloride gas in sufficient amount to provide an excess of said hydrogen chloride reactant in said reactor and recovering a reaction product containing said monochloroalkane or monochlorocycloalkane issuing from said reactor.

2. A method according to claim 1 in which said reaction product is separated into an upper and a lower layer and said monochloroalkane or monochlorocycloalkane recovered in said upper layer.

3. A method according to claim 1 in which said reacting is conducted at a temperature ranging from 60° to 97° C.

4. A method according to claim 1 in which said aqueous zinc chloride solution consists of at least about 70 weight percent zinc chloride.

5. A method according to claim 1 in which said mixture consists of from 1.5 to 3 parts by weight of said aqueous zinc chloride solution and 1 part by weight of said alcohol.

6. A method according to claim 1 in which the amount of said gaseous hydrogen chloride amounts to at least 5% excess over the amount required for stoichmetrical reaction with said monohydric alcohol.

7. A method according to claim 1 in which said alcohol is cyclohexanol.

8. A method according to claim 1 in which said alcohol in n-dodecanol.

* * * * *